(12) United States Patent
Bai et al.

(10) Patent No.: US 11,602,734 B2
(45) Date of Patent: Mar. 14, 2023

(54) ACID/METAL BIFUNCTIONAL CATALYSTS PRODUCED BY SLURRY METHODS

(71) Applicant: ExxonMobil Technology and Engineering Company, Annandale, NJ (US)

(72) Inventors: Chuansheng Bai, Phillipsburg, NJ (US); Majosefina Cunningham, Whitehall, PA (US); Jihad M. Dakka, Whitehouse Station, NJ (US); Preeti Kamakoti, Berkeley Heights, NJ (US); Aruna Ramkrishnan, Bridgewater, NJ (US); Anjaneya S. Kovvali, Herndon, VA (US); Anita S. Lee, Spring, TX (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 1 day.

(21) Appl. No.: 16/993,219

(22) Filed: Aug. 13, 2020

(65) Prior Publication Data

US 2021/0046462 A1 Feb. 18, 2021

Related U.S. Application Data

(60) Provisional application No. 62/886,989, filed on Aug. 15, 2019.

(51) Int. Cl.

| | |
|---|---|
| *B01J 29/06* | (2006.01) |
| *B01J 23/80* | (2006.01) |
| *C07C 41/01* | (2006.01) |
| *B01J 29/46* | (2006.01) |
| *B01J 27/188* | (2006.01) |
| *B01J 27/19* | (2006.01) |
| *B01J 35/02* | (2006.01) |
| *B01J 35/10* | (2006.01) |
| *B01J 37/04* | (2006.01) |
| *B01J 37/08* | (2006.01) |
| *B01J 37/10* | (2006.01) |
| *B01J 37/00* | (2006.01) |
| *B01J 37/18* | (2006.01) |
| *B01J 21/04* | (2006.01) |
| *C07C 31/04* | (2006.01) |
| *C07C 43/04* | (2006.01) |
| *C07C 29/154* | (2006.01) |

(52) U.S. Cl.
CPC ............ *B01J 23/80* (2013.01); *B01J 21/04* (2013.01); *B01J 27/188* (2013.01); *B01J 27/19* (2013.01); *B01J 29/46* (2013.01); *B01J 35/026* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 35/1061* (2013.01); *B01J 37/0036* (2013.01); *B01J 37/04* (2013.01); *B01J 37/082* (2013.01); *B01J 37/10* (2013.01); *B01J 37/18* (2013.01); *C07C 29/154* (2013.01); *C07C 31/04* (2013.01); *C07C 41/01* (2013.01); *C07C 43/043* (2013.01)

(58) Field of Classification Search
CPC .. Y02P 20/52; B01J 21/04; B01J 23/80; B01J 2229/186; B01J 27/18; B01J 27/188; B01J 27/198; B01J 27/199; B01J 27/195; B01J 29/46; B01J 29/405; B01J 29/42; B01J 29/44; B01J 29/48; B01J 29/82; B01J 35/026; B01J 35/1014; B01J 35/1019; B01J 35/1038; B01J 35/1042; B01J 35/1047; B01J 35/1061; B01J 35/002; B01J 37/0036; B01J 37/04; B01J 37/082; B01J 37/08; B01J 37/18; B01J 37/10; C07C 29/154; C07C 41/01; C07C 43/043; C07C 31/04
USPC ....... 502/60, 73, 74, 77, 208, 210, 211, 213, 502/305, 306, 307, 308, 309, 311, 312, 502/313, 314, 316, 317, 318, 319, 320, 502/321, 341, 342, 343, 345, 346, 350, 502/351, 353, 354, 355; 518/713
See application file for complete search history.

(56) References Cited

U.S. PATENT DOCUMENTS

| | | | |
|---|---|---|---|
| 5,218,003 | A | 6/1993 | Lewnard et al. |
| 6,069,107 | A | 5/2000 | Kuznetsov et al. |
| 2012/0157554 | A1 | 6/2012 | Okuyama et al. |
| 2013/0030224 | A1 | 1/2013 | Kim et al. |
| 2013/0211147 | A1 | 8/2013 | Cheiky et al. |
| 2016/0347906 | A1 | 12/2016 | Williams et al. |

FOREIGN PATENT DOCUMENTS

| | | |
|---|---|---|
| CN | 101485983 A | 7/2009 |
| CN | 104646049 A | 5/2015 |

(Continued)

OTHER PUBLICATIONS

Bae et al., "Coproduction of MeOH and DME from Biomass-Derived Syngas on a Cu—ZnO—Al2O3/Al2O3 Hybrid Catalyst", Energy and Fuels, vol. 22, No. 1, 2008, pp. 223-230.*

(Continued)

*Primary Examiner* — Elizabeth D Wood
(74) *Attorney, Agent, or Firm* — Shook, Hardy & Bacon L.L.P.

(57) ABSTRACT

A method of producing a acid/metal bifunctional catalyst may include: mixing an acid catalyst, a metal catalyst, and a fluid to produce a slurry, wherein the acid catalyst is present at 50 wt % or less relative to a total catalyst weight in the slurry; heating the slurry; producing a powder from the slurry; and calcining the powder to produce the acid/metal bifunctional catalyst. Such acid/metal bifunctional catalyst would be useful in the direct conversion of syngas to dimethyl ether as well as other reactions.

19 Claims, 6 Drawing Sheets

(56) References Cited

FOREIGN PATENT DOCUMENTS

| CN | 104069856 B | 4/2016 |
|----|-------------|--------|
| CN | 106536045 A | 3/2017 |
| JP | 2003-38957 A | 2/2003 |
| WO | 2005/046855 A2 | 5/2005 |

OTHER PUBLICATIONS

Zhang et al., "Improvement of a Mesh-Type Cu/Ni/Al2O3/Al Catalyst for Steam Reforming of Dimethyl Ether by Metal (Fe, Zn or La) Addition for Co in Situ Removal", Modern Research in Catalysis, 2018, 7, pp. 1-16.*

Final Office Action dated Jan. 12, 2023 in U.S. Appl. No. 16/947,704, 15 pages.

Kamata, H., et al., "Steam Reforming of Dimethyl Ether over Cu/ZnO/ZrO2 and γ-Al2O3 Mixed Catalyst Prepared by Extrusion", Journal of the Japan Petroleum Institute, vol. 51, No. 3, pp. 157-164 (2008).

Non-Final Office Action dated Jul. 21, 2022 in U.S. Appl. No. 16/947,699, 12 pages.

Non-Final Office Action dated Aug. 4, 2022 in U.S. Appl. No. 16/947,704, 14 pages.

Non-Final Office Action dated Aug. 23, 2022 in U.S. Appl. No. 16/947,701, 10 pages.

Non-Final Office Action dated Sep. 15, 2022 in U.S. Appl. No. 16/947,706, 8 pages.

\* cited by examiner

ACID/METAL BIFUNCTIONAL CATALYSTS PRODUCED BY SLURRY METHODS

CROSS REFERENCE TO RELATED APPLICATIONS

This application claims priority to U.S. Provisional Application Ser. No. 62/886,989 filed Aug. 15, 2019, which is herein incorporated by reference in its entirety.

FIELD

The present disclosure relates to catalysts for direct conversion of syngas to dimethyl ether.

BACKGROUND

Various processes have been proposed for producing dimethyl ether from natural gas. One such process involves co-feeding natural gas with an enriched oxygen stream to an autothermal reformer to produce syngas. Dimethyl ether may then be produced in a two-stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether in a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

A newer method has been developed for a one-stage process of converting syngas to dimethyl ether. The newer method uses two separate catalysts in a single reactor to convert CO and $H_2$ to methanol with a metal catalyst and the methanol to dimethyl ether with an acid second catalyst. However, the size of the two catalysts are different. Accordingly, when physically mixing the catalysts, the two types of catalysts would segregate because of the size differences. Such segregation can lead to conversion inefficiencies.

SUMMARY

The present disclosure relates to bifunctional catalysts and methods of producing such bifunctional catalysts that combine the functionality of an acid catalyst and a metal catalyst. Such acid/metal bifunctional catalyst would be useful in the direct conversion of syngas to dimethyl ether as well as other reactions.

A method of the present disclosure may include: mixing an acid catalyst, a metal catalyst, and a fluid to produce a slurry, wherein the acid catalyst is present at 50 wt % or less relative to a total catalyst weight in the slurry; heating the slurry; drying the slurry to produce a dried slurry; producing a powder from the dried slurry; and calcining the powder to produce an acid/metal bifunctional catalyst.

A method of the present disclosure may include: activating an acid/metal bifunctional catalyst in the presence of hydrogen at 150° C. to 350° C., wherein the acid/metal bifunctional catalyst has an average diameter of 0.01 µm to 100 µm and comprises an acid catalyst component and a metal catalyst component, wherein the acid catalyst component is selected from the group consisting of a zeolite, an ion exchanged zeolite, a molecular sieve, a metal oxide, and any combination thereof, wherein the metal catalyst component is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different, and the acid catalyst component is present at 50 wt % or less relative to the acid/metal bifunctional catalyst; and reacting the activated acid/metal bifunctional catalyst with a feedstream comprising hydrogen and carbon monoxide.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to bifunctional catalysts and methods of producing such bifunctional catalysts that combine the functionality of a metal catalyst and an acid catalyst. Such acid/metal bifunctional catalysts would be useful in the direct conversion of syngas to dimethyl ether as well as other reactions. Further, because a single catalyst particle is used, the segregation issue with two catalyst particle sizes is mitigated, and the catalyst bed has a more homogeneous distribution of the acid catalyst functionality and the metal catalyst functionality.

Previous attempts to combine the functionality of a metal catalyst and an acid catalyst into a single bifunctional catalyst had issues. For example, the acid portion of the bifunctional catalyst produces coke that deactivates the metal portion. Further, the metal portion tends to migrate along the surface of the catalyst support to areas where the acid portion is and poison or deactivate the acid portion of the bifunctional catalyst. The methods of the present disclosure for making acid/metal bifunctional catalysts in a straightforward manner where the relative amounts of each portion of the catalyst can be adjusted.

Acid/Metal Bifunctional Catalysts

The acid/metal bifunctional catalysts of the present disclosure are produced by slurry mixing to deposit acid catalyst particles on metal catalyst particles. Generally, in slurry mixing the two individual particles are mixed and heated in a fluid. The fluid is then at least substantially evaporated to produce a powder that is calcined to produce the acid/metal bifunctional catalysts.

Figure 1:
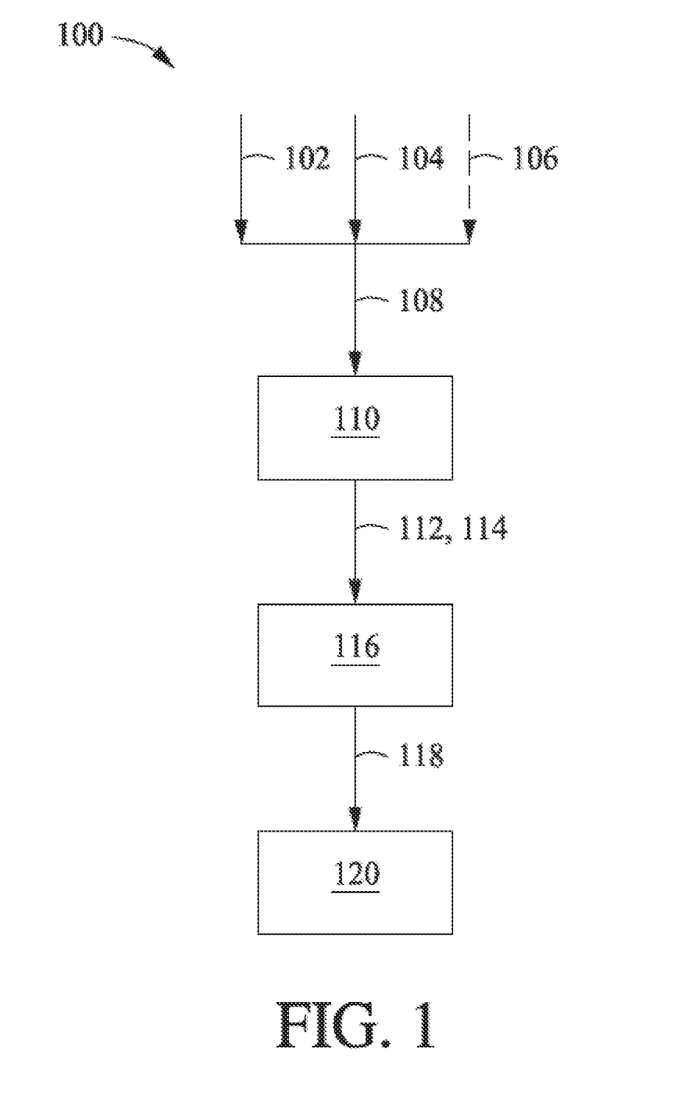
FIG. 1 is a flowchart illustrating an example method of preparing acid/metal bifunctional catalyst.

FIG. 1 is a flowchart illustrating an example method 100 of preparing an acid/metal bifunctional catalyst. The method includes mixing 108 an acid catalyst 102, a metal catalyst 104, and a fluid 106 to produce a slurry 110. Optionally, the acid catalyst 102 and/or the metal catalyst 104 can be dispersed in the fluid 106 before mixing, in which additional fluid may or may not be needed for producing the slurry 110. For example, the acid catalyst 102 may be dispersed in a first fluid and the metal catalyst 104 may be dispersed in second fluid, where the first and second fluids may be the same or different. Then, mixing the acid catalyst 102, the metal catalyst 104, and the fluid 106 may be achieved by adding the acid catalyst 102 dispersed in a first fluid into the metal catalyst 104 dispersed in second fluid, or vice versa. Alternatively, only one of the acid catalyst 102 and the metal catalyst 104 may be dispersed in a fluid. Then, mixing the acid catalyst 102, the metal catalyst 104, and the fluid 106 may be achieved by adding dry catalyst into the dispersed catalyst, or vice versa. Alternatively, both the acid catalyst 102 and the metal catalyst 104 may be dry and either added as a mixture or individually to the fluid 106.

Preferably, the metal catalyst 104 is at a higher percent based on the total catalyst weight in the slurry 110. The metal catalyst 104 may be present in the slurry 110 at about 50 wt % or greater (or about 50 wt % to 90 wt %, or 65 wt % to 85 wt %) based on the total catalyst weight in the slurry 110. The acid catalyst 102 may be present in the slurry 110 at about 50 wt % or less (or about 10 wt % to 50 wt %, or 15 wt % to 35 wt %) based on the total catalyst weight in the slurry 110.

Optionally, the slurry 110 may further comprise inert particles up to about 50 wt % (or about 1 wt % to about 50 wt %, or about 5 wt % to about 25 wt %, or about 20 wt % to about 50 wt %) based on a total solids weight in the slurry 110.

The acid catalyst 102 may be any acid catalyst suitable for converting methanol to dimethyl ether. Generally, the acid property of the acid catalyst 102 may be Lewis acidity, Bronsted acidity, or the combination of both Lewis acidity and Bronsted acidity. Examples of acid catalysts 102 can include, but are not limited to, a zeolite, an ion exchanged zeolite, molecular sieves (e.g., SAPO), metal oxides (e.g., oxides of aluminum, silicon, zirconium, boron, and combinations thereof like alumiosilicates, boroaluminosilicates, borosilicates, and the like), and any combination thereof. Examples of zeolites can include, but are not limited to, MCM-49, HZSM-5-5B, mordenite, ZSM-35, ZSM-48, ZSM-11, Chabazite, boric acid modified alumina, phosphorus oxide modified alumina, ERS-8, MoPOx, and the like, and any combination thereof. Examples of combinations of acid catalyst include, but are not limited to, $WO_3$, $ZrO_2$, $SiO_2$, resins, metal organic frameworks (MOFs), zeolite imidazolate frameworks (ZIFs), and the like, and any combination thereof.

The metal catalyst 104 may be any metal catalyst suitable for converting CO and $H_2$ to methanol. Examples of metal catalysts 104 can include, but are not limited to, a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

The acid catalyst 102 preferably has a larger particle size than the metal catalyst 104. This allows for the metal catalyst 104 to be deposited on the acid catalyst 102. The acid catalyst 102 may have an average diameter (determined by light scattering) of about 1 μm to about 100 μm, or about 1 μm to about 25 μm, or about 20 μm to about 50 μm, or about 25 μm to about 75 μm, or about 50 μm to about 100 μm. The metal catalyst 104 may have an average diameter (determined by light scattering) of about 0.01 μm to about 10 μm, or about 0.01 μm to about 1 μm, or about 0.1 μm to about 2 μm, or about 1 μm to about 5 μm, or about 2 μm to about 10 μm.

The fluid 106 may be present in the slurry 110 in a sufficient amount to disperse the acid catalyst 102 and the metal catalyst 104 and form the slurry 110. The fluid 106 can be any fluid or mixture of fluids suitable for suspending the acid catalyst 102 and the metal catalyst 104. Examples of fluids 106 can include, but are not limited to, water, methanol, ethanol, alcohols of $C_1$ to $C_{10}$, oxygenates, and the like, and any combination thereof.

Once the slurry 110 is produced, the method may further include heating 112 the slurry 110. Heating may be to a temperature of about 50° C. to about 120° C. (or about 65° C. to about 100° C., or about 75° C. to about 95° C.). Further, heating may be to a temperature that is within about 20° C. (or about 10° C.) of a boiling point of the fluid 106.

Mixing 108 to produce the slurry 110 before heating 112 may occur for any suitable amount of time (e.g., seconds to minutes to hours or longer) and at any suitable rate to produce the slurry 110 where the acid catalyst 102 and the metal catalyst 104 are substantially homogeneously dispersed in the fluid 106. For example, mixing 108 may occur for 5 minutes to 3 hours at a vigorous rate before heating 112.

Preferably, the method includes mixing the slurry 110 while heating 112 the slurry 110 so that the acid catalyst 102 and the metal catalyst 104 do not settle. Heating 112 the slurry 110 may occur for any suitable amount of time (e.g., seconds to minutes to hours or longer) and at any suitable mixing rate (if mixed) to maintain a dispersion. For example, heating 112 may occur for 5 minutes to 3 hours at a vigorous rate while the slurry is at an elevated temperature.

Next, the method 100 includes producing 114 a powder 116 from the slurry 110. Generally, to produce a powder 116, the liquid 106 is at least substantially removed from the solids (the catalyst particles 102, 104 in this example). Removal of the liquid 106 can be by evaporation, filtration, and the like, and any combination thereof. Accordingly, the process of producing 114 the powder 116 can include the heating step 112. For example, the heating step 112 may be performed so that at least a portion of the liquid 106 evaporates from the slurry 110.

When the liquid 106 is at least substantially removed, the resultant product may clump together. Accordingly, methods to produce a finer powder that has suitable surface area for a fixed bed reactor may be carried out as part of the producing 114 step. For example, grinding, crumbling, ball milling, and the like, and any combination thereof can be used.

Preferably, the powder 116 is substantially dry and has a dampness (or fluid content) such that the powder 116 comprises the fluid 106 at about 5 wt % or less (or 0 wt % to about 5 wt %, or 0 wt % to about 3 wt %, or about 0.1 wt % to about 3 wt %, or 0 wt % to about 1 wt %).

To reduce the amount of fluid 106 in the powder 116, the solids after initial steps to remove the liquid 106 (e.g., evaporation, filtration, and the like, and any combination thereof) can be dried at elevated temperatures. Such temperatures should be lower than a temperature that would cause significant calcining of the solids. For example, drying may occur in an inert gas (e.g., nitrogen, argon, and the like, and any combination thereof) or oxygen-containing gas (e.g., oxygen, air, oxygen-enriched air, and the like) at temperature of about 50° C. to about 120° C. (or about 65° C. to about 100° C., or about 75° C. to about 95° C.) for a suitable amount of time (e.g., about 10 minutes to about 48 hours, or about 1 hour to about 24 hours, or about 8 hours to about 18 hours) to achieve a desired amount of fluid 106 in the powder 116.

Then, the method 100 includes calcining 118 the powder 116 to produce the acid/metal bifunctional catalyst 120. Calcining may occur in an oxygen-containing gas (e.g., oxygen, air, oxygen-enriched air, and the like) at a temperature of about 200° C. to about 400° C. (or about 250° C. to about 350° C., or about 275° C. to about 375° C.) for any suitable amount of time (e.g., about 10 minutes to about 48 hours, or about 30 minutes to about 24 hours, or about 1 hour to about 12 hours, or about 1 hour to about 6 hours).

Preferably, the metal catalyst 104 component is at a higher percent based on the total acid/metal bifunctional catalyst 120 weight. The metal catalyst 104 component may be present in the acid/metal bifunctional catalyst 120 at about 50 wt % or greater (or about 50 wt % to 90 wt %, or 65 wt % to 85 wt %) based on the total acid/metal bifunctional catalyst 120 weight. The acid catalyst 102 component may be present in the acid/metal bifunctional catalyst 120 at about 50 wt % or less (or about 10 wt % to 50 wt %, or 15 wt % to 35 wt %) based on the total acid/metal bifunctional catalyst 120 weight. Optionally, the acid/metal bifunctional catalyst 120 may further comprise an inert component, derived from the inert particles, present at up to about 50 wt % (or about 1 wt % to about 50 wt %, or about 5 wt % to about 25 wt %, or about 20 wt % to about 50 wt %) based on a total acid/metal bifunctional catalyst 120 weight.

The acid/metal bifunctional catalyst 120 particles may have an average diameter (determined by light scattering) of about 0.01 μm to about 100 μm, or about 1 μm to about 100 μm, or about 1 μm to about 25 μm, or about 20 μm to about 50 μm, or about 25 μm to about 75 μm, or about 50 μm to about 100 μm. Optionally, after the acid/metal bifunctional catalyst 120 is formed, grinding or any suitable method can be used to achieve a desired particle size.

The acid/metal bifunctional catalyst 120 particles may have a $N_2$ BET surface area according to ASTM D3663-03 (2015) of about 75 $m^2/g$ to about 200 $m^2/g$ (about 90 $m^2/g$ to about 185 $m^2/g$, or about 100 $m^2/g$ to about 170 $m^2/g$).

The acid/metal bifunctional catalyst 120 particles may have an average pore volume according to $N_2$ BET about 0.1 mL/g to about 1.2 mL/g (or about 0.2 mL/g to about 0.75 mL/g, or about 0.3 mL/g to about 0.6 mL/g).

The acid/metal bifunctional catalyst 120 particles may have an average pore size according to ASTM D4641-17 of about 7 nm to about 17 nm (or about 8 nm to about 16 nm, or about 9 nm to about 15 nm).

The acidity of the acid/metal bifunctional catalyst 120 particles measured with pyridine for Bronsted acid cites (1545 $cm^{-1}$ and 1450 $cm^{-1}$ infrared spectra bands) and ammonia for Lewis acid cites (1620 $cm^{-1}$ and 1450 $cm^{-1}$ infrared spectra bands) may be cumulatively about 1 site to about 250 sites, or 25 sites to 200 sites, or 50 sites to 150 sites.

Direct Synthesis of Dimethyl Ether from Syngas

Figure 2:
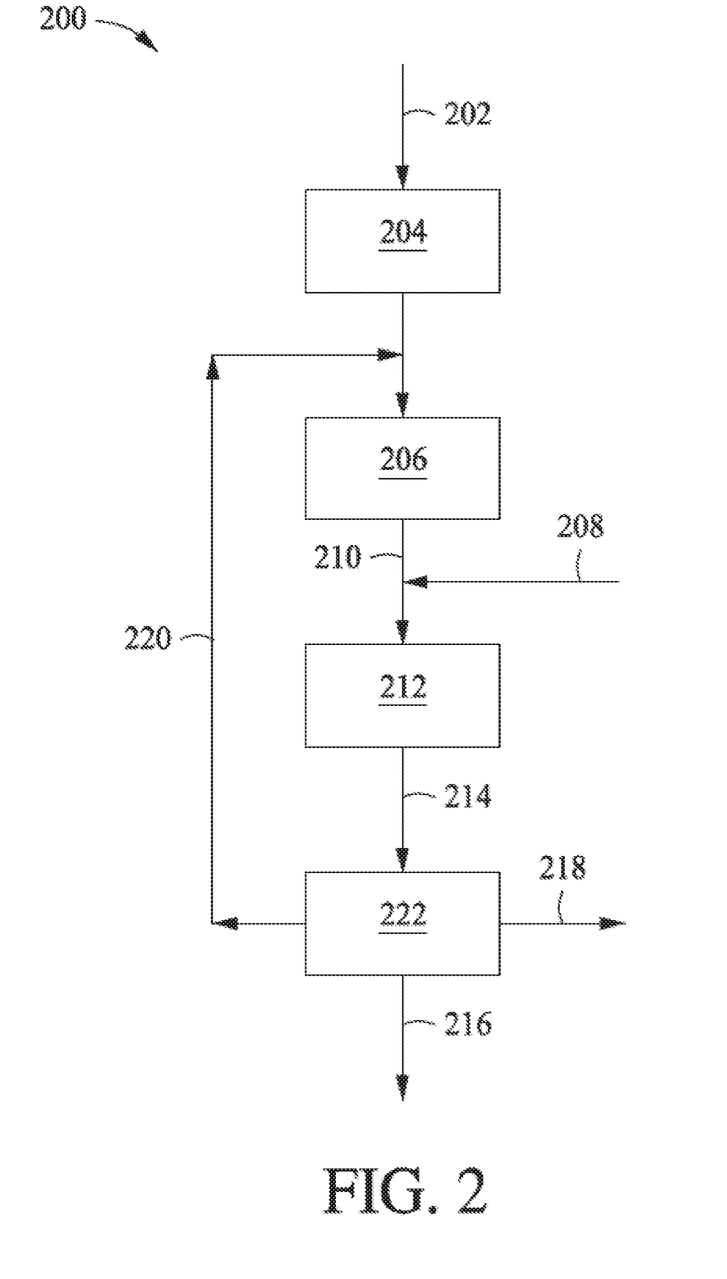
FIG. 2 is a flowchart illustrating an example integrated system and process for producing dimethyl ether from natural gas according to one or more embodiments of the present invention.

An example 200 method and system for the production of dimethyl ether from natural gas is illustrated in FIG. 2. A natural gas stream 202 is fed to a pretreater 204 to remove contaminants such as sulfur, chlorides and olefins. The pretreater 204 may be a single unit or, more likely, it is a series of units for removing the different types of contaminants found in the natural gas stream 204. For example, the pretreater 204 may include a desulfurizing column for removing sulfur. The pretreater 204 can also include a guard bed to remove chlorides and/or a hydrotreater to covert olefins to paraffins.

The pretreated natural gas may then be fed to a reformer 206, which may be a reverse flow reactor, to convert the natural gas to a syngas 210. A recycled $CO_2$ stream 220, which may also include recycled methane, can be fed with the treated natural gas to the reformer 206. It is noted that the pretreated natural gas stream may contain essentially zero $CO_2$ (such as the gas in pipeline gas) or it may have a high $CO_2$ content. Steam may also be added to the reformer 206 to promote the conversion of natural gas to syngas.

Steam 208 and syngas 210 are co-fed to a dimethyl ether reactor 212 to produce a product stream 214, which can include dimethyl ether, carbon dioxide, methane, hydrogen, and other byproducts. The dimethyl ether reactor 212 may operate at a temperature of about 200° C. to about 300° C. (or about 230° C. to about 270° C.), a pressure of about 20 bar to about 50 bar (or about 30 bar to about 40 bar), and a gas hourly space velocity (GHSV) of about 1,000 $hr^{-1}$ to about 8,000 $hr^{-1}$ (or about 1,500 $hr^{-1}$ to about 3,000 $hr^{-1}$).

The product stream 214 may be fed to one or more separators 222 to separate the methane, carbon dioxide, and other byproducts 218 from dimethyl ether 216. Methane and carbon dioxide may be recycled back to the reformer 206 via the recycle stream 28. The separation of the products may be accomplished using various separation processes including refrigeration, distillation/fractionation, high-pressure or low-pressure flash separation, or membrane separation.

Prior to running the foregoing method, the acid/metal bifunctional catalyst may be activated by exposure to hydrogen at elevated temperatures (e.g., about 150° C. to about 350° C., or about 200° C. to about 300° C.).

Direct dimethyl ether synthesis may be performed by converting syngas to methanol (Eq. 1) with the in-situ dehydration of methanol to dimethyl ether (Eq. 3). Advantageously, both reactions can occur in the same reactor such that the methanol is nearly instantaneously dehydrated to dimethyl ether as it is produced. In addition, a water gas shift reaction (Eq. 2) is typically present.

$$CO + 2H_2 \leftrightarrow CH_3OH \quad \Delta H_r = -90.84 \text{ kJ/mole} \quad \text{(Eq. 1)}$$

$$CO + H_2O \leftrightarrow CO_2 + H_2 \quad \Delta H_r = -41.27 \text{ kJ/mole} \quad \text{(Eq. 2)}$$

The equilibrium of the methanol reaction (Eq. 1) at high temperatures required to promote kinetics, is reactant favored and limits the overall syngas conversion in a traditional methanol process. However, the disclosed acid/metal bifunctional catalyst may enable the in-situ dehydration of methanol immediately after it is formed, which maintains the system sufficiently far from equilibrium limitations of Eq. 1 and may improve the per-pass conversion of syngas.

Various by-products can also be produced during the conversion of syngas to methanol (e.g., methane, water, carbon dioxide, formic acid) and the conversion of methanol to dimethyl ether (e.g., acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of $CO_2$ in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the acid/metal bifunctional catalyst stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3-O-CH_3 + H_2O \ \Delta H_r = -21.26 \text{ kJ/mole} \quad \text{(Eq. 3)}$$

$$3CO + 3H_2 \leftrightarrow CH_3-O-CH_3 + CO_2 \ \Delta H_r = -246 \text{ kJ/mole} \quad \text{(Eq. 4)}$$

It has been found that carbon efficiency can be improved by controlling feed parameters, particularly the amount of water added to either the reforming reactor or the dimethyl ether reactor. Conventionally, syngas conversion process uses factors like $H_2$:CO ratio or M-value, which is $(H_2-CO_2)/(CO+CO_2)$, to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in an amount to leverage the water-gas-shift reaction to co-produce $CO_2$ (as needed to maximize carbon efficiency) in the dimethyl ether reactor. The amount of water added is a function of the syngas composition (namely the amount of $CO/CO_2/H_2/H_2O$ present in the feed to the dimethyl ether reactor), which is a function of the steam reforming relative to the dry reforming carried out in the syngas reactor.

A preferred feed to the dimethyl ether reactor may be described with a modified M-value (Mm) per the following equation.

$$Mm = \frac{H_2 - CO_2 + H_2O}{CO + CO_2 - H_2O}$$

Water may be added to the process in total, either in the syngas reactor for steam reforming or in the dimethyl ether reactor. Independent of how the water is split between the reactors this corresponds to a modified M-value of about 1.4 to 1.8 (or 1.5 to 1.7, or 1.6).

Various reforming processes may be employed to produce syngas from such a natural gas feedstream including, but not limited to, partial oxidation, steam methane reforming, autothermal reforming, dry reforming, and the like, and any combination thereof. Preferably, the natural gas stream is reformed using a reverse flow reactor.

Any natural gas feedstream can be reformed into syngas. As used herein, "natural gas" refers to a hydrocarbon feed that is predominantly $C_1$ to $C_4$ hydrocarbons, and it may be predominantly methane. The natural gas feedstream can also include carbon dioxide. For simplicity, examples used herein may make specific reference to methane; however, it should be understood that natural gas feed streams further comprising $C_2$-$C_4$ hydrocarbons may also be used. General equations for the dry reforming and steam reforming for such hydrocarbons are shown in Eq. 5 and Eq. 6, respectively.

$$C_nH_{2n+1} + CO_2 \rightarrow 2nCO + (n+1)H_2 \quad \text{(Eq. 5)}$$

$$C_nH_{2n+1} + H_2O \rightarrow nCO + (2n+1)H_2 \quad \text{(Eq. 6)}$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of $CO_2$ and 2 moles of methane may produce 4 moles of CO and 4 moles of $H_2$ as shown in Eq. 7.

$$2CO_2 + 2CH_4 \leftrightarrow 4CO + 4H_2 \quad \text{(Eq. 7)}$$

If the products of Eq. 5 were then fed to the dimethyl ether reactor with steam as a co-feed, the following products would be produced: 1 mole of dimethyl ether, 2 moles of $CO_2$ and 1 mole of $H_2$ (Eqs. 4 and 2).

The reverse flow reactor for reforming the natural gas to syngas may operate at a temperature of about 300° C. and about 1400° C. (or about 500° C. and about 1000° C.) and a pressure range of about 1 bar and about 100 bar (or about 10 bar to about 50 bar).

The effluent from the dimethyl ether reactor may be separated into dimethyl ether, $CO_2$ (optionally with any unreacted $CH_4$, CO, and/or $H_2$), and other byproducts. Any one or combination of separation processes may be employed to perform such separations including, but not limited to, refrigeration, distillation/fractionation, flash separation and membrane separation. The $CO_2$, $CH_4$, and any unreacted intermediates may be recycled as described herein.

Advantageously, recycle streams having desirable compositions can be obtained from separation processes downstream of the dimethyl ether reactor. These recycle streams can be used to improve the carbon efficiency of the integrated system and/or can provide other advantages.

In any embodiment, $CO_2$ and $CH_4$, and optionally CO, recovered downstream of the dimethyl ether reactor may be recycled upstream of the syngas generation reactor. The $CO_2$ may be provided in sufficient quantities such that when added to the $CO_2$ native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the $CO_2$ and $CH_4$, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

Example Embodiments

A first nonlimiting example embodiment of the present disclosure is a method comprising: mixing an acid catalyst, a metal catalyst, and a fluid to produce a slurry, wherein the acid catalyst is present at 50 wt % or less relative to a total catalyst weight in the slurry; heating the slurry; drying the slurry to produce a dried slurry; producing a powder from the dried slurry; and calcining the powder to produce an acid/metal bifunctional catalyst. Such embodiment may optionally further comprise one or more of the following: Element 1: wherein producing the powder from the dried slurry comprises: grinding the dried slurry to produce a powder, wherein the powder comprises 5 wt % or less of the fluid; Element 2: wherein mixing is maintained during heating; Element 3: wherein mixing is performed for 30 minutes to 3 hours; Element 4: wherein heating is to a temperature within 20° C. of a boiling point of the fluid; Element 5: wherein the acid catalyst is selected from the group consisting of a zeolite, an ion exchanged zeolite, a molecular sieve, a metal oxide, and any combination thereof; Element 6: wherein the metal catalyst is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different; Element 7: wherein the acid catalyst is present at 10 wt % to 50 wt % relative to the total catalyst weight in the slurry; Element 8: wherein the acid catalyst is present at 15 wt % to 35 wt % relative to the total catalyst weight in the slurry; Element 9: wherein the acid catalyst has a larger average diameter than the metal catalyst; Element 10: wherein the fluid is selected from the group consisting of: water, methanol, ethanol, alcohols of C1 to C10, oxygenates, and any combination thereof; Element 11: wherein calcining is performed in air at 200° C. to 400° C.; Element 12: wherein the acid/metal bifunctional catalyst has an average diameter of 0.01 μm to 100 μm; Element 13: wherein the acid/metal bifunctional catalyst has a $N_2$ BET surface area according to ASTM D3663-03 (2015) of about 75 m$^2$/g to about 200 m$^2$/g; Element 14: wherein the acid/metal bifunctional catalyst has an average pore volume of about 0.1 mL/g to about 1.2 mL/g; Element 15: wherein the acid/metal bifunctional catalyst has an average pore size according to ASTM D4641-17 of about 7 nm to about 17 nm; Element 16: the method further comprising: activating the acid/metal bifunctional catalyst in the presence of hydrogen at 150° C. to 350° C.; and reacting the activated acid/metal bifunctional catalyst with a feedstream comprising hydrogen and carbon monoxide; Element 17: Element 16 and wherein reacting is at a temperature of about 200° C. to about 300° C., a pressure of about 20 bar to about 50 bar, and a gas hourly space velocity (GHSV) of about 1,000 hr$^{-1}$ to about 8,000 hr'; Element 18:

Element 16 and wherein the reacting the activated acid/metal bifunctional catalyst with the feedstream is in the presence of steam; Element 19: Element 16 and wherein reacting the activated acid/metal bifunctional catalyst with the feedstream has a selectivity to producing methanol of 25% to 60%; and Element 20: Element 16 and wherein reacting the activated acid/metal bifunctional catalyst with the feedstream has a selectivity to producing dimethyl ether of 20% to 55%. Examples of combinations include, but are not limited to, two or more of Elements 1-4 in combination; two or more of 5-10 in combination; Element 11 in combination with one or more of Elements 1-4; one or more of Elements 1, 2, 3, 4, or 11 in combination with one or more of Elements 5-10; two or more of Elements 12-15 in combination; one or more of Elements 12-15 in combination with one or more of Elements 1-11; one or more of Elements 1-15 in combination with Element 16 and optionally in further combination with one or more of Elements 17-20; and Element 16 in combination with two or more of Elements 17-20.

A second nonlimiting example embodiment of the present disclosure is a method comprising: activating an acid/metal bifunctional catalyst in the presence of hydrogen at 150° C. to 350° C., wherein the acid/metal bifunctional catalyst has an average diameter of 0.01 μm to 100 μm and comprises an acid catalyst component and a metal catalyst component, wherein the acid catalyst component is selected from the group consisting of a zeolite, an ion exchanged zeolite, a molecular sieve, a metal oxide, and any combination thereof, wherein the metal catalyst component is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different, and the acid catalyst component is present at 50 wt % or less relative to the acid/metal bifunctional catalyst; and reacting the activated acid/metal bifunctional catalyst with a feedstream comprising hydrogen and carbon monoxide. Such embodiment may optionally further comprise one or more of the following: Element 12; Element 13; Element 14; Element 15; Element 17; Element 18; Element 19; and Element 20.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Preparation of 25 wt % CATAPAL® Al$_2$O$_3$ mixed with 75 wt % CuZnAl (Reference)

6.58 g of CATAPAL® γ-alumina (LOI % 76%, 5.00 g of Al$_2$O$_3$) was mixed with 15.00 g of commercial methanol catalyst of CuZnAl powders (from Clariant). The methanol was evaporated.

Preparation of 25 wt % CATAPAL® Al$_2$O$_3$/CuZnAl (Sample 1)

6.58 g of CATAPAL® γ-alumina (LOI % 76%, 5.00 g of Al$_2$O$_3$) were dispersed in 60 g of distilled water. The slurry was under vigorous stirring for 30 min. 15.00 g of commercial methanol catalyst of CuZnAl powders were added into the slurry. The slurry was kept vigorously stirring for another 30 min. Then, the slurry was heated with continued stirring in a water-bath with temperature maintained at 80° C. to 90° C. The slurry was kept stirring in the water bath until it was close to dryness. The sample was then dried at 120° C. in air for 16 hours. The powdery sample was ground in a fume hood for 10 min. After grinding, the sample was placed in a box furnace. The furnace was ramped from room temperature to 300° C. at a rate of 10° F./min (5.6° C./min) in air. The air flowing rate was set at 5 volume/volume catalyst/minute. The samples were held at 300° C. in air for 3 hrs.

Preparation of 25 wt % ZSM-5/CuZnAl (Sample 2)

5.00 g of ZSM-5 were dispersed in 60 g of distilled water. The slurry was under vigorous stirring for 30 min. 15.00 g of commercial methanol catalyst of CuZnAl powders were added into the slurry. The slurry was kept vigorously stirring for another 30 min. Then, the slurry was heated with continued stirring in a water-bath with temperature maintained at 80° C. to 90° C. The slurry was kept stirring in the water bath until it was close to dryness. The sample was then dried at 120° C. in air for 16 hours. The powdery sample was ground in a fume hood for 10 min. After grinding, the sample was placed in a box furnace. The furnace was ramped from room temperature to 300° C. at rate of 10° F./min (5.6° C./min) in air. The air flowing rate was set at 5 volume/volume catalyst/minute. The samples were held at 300° C. in air for 3 hrs.

Preparation of 25 wt % WPOx/CuZnAl (Sample 3)

5.177 g of phosphotungstic acid hydrate was dissolved in 60 g of distilled $H_2O$. The mixture was kept stirring until the solution became clear. 15.00 g of commercial methanol catalyst of CuZnAl powders were added into the solution. The resultant slurry was kept stirring for another 30 min. Then, the slurry was heated with continued stirring in a water-bath with temperature maintained at 80° C. to 90° C. The slurry was kept stirring in the water bath until it was close to dryness. The sample was then dried at 120° C. in air for 16 hours. The powdery sample was ground in a fume hood for 10 min. After grinding, the sample was placed in a box furnace. The furnace was ramped from room temperature to 300° C. at rate of 10° F./min (5.6° C./min) in air. The air flowing rate was set at 5 volume/volume catalyst/minute. The samples were held at 300° C. in air for 3 hrs.

Preparation of 25 wt % MoPOx/CuZnAl (Sample 4)

5.177 g of ammonium phosphomolybdate hydrate was dissolved in 60 g of distilled $H_2O$. The mixture was kept stirring until the solution became clear. 15.00 g of commercial methanol catalyst of CuZnAl powders were added into the solution. The resultant slurry was kept stirring for another 30 min. Then, the slurry was heated with continued stirring in a water-bath with temperature maintained at 80° C. to 90° C. The slurry was kept stirring in the water bath until it was close to dryness. The sample was then dried at 120° C. in air for 16 hours. The powdery sample was ground in a fume hood for 10 min. After grinding, the sample was placed in a box furnace. The furnace was ramped from room temperature to 300° C. at rate of 10° F./min (5.6° C./min) in air. The air flowing rate was set at 5 volume/volume catalyst/minute. The samples were held at 300° C. in air for 3 hrs.

Catalysts Properties

The properties (determined by $N_2$ BET) of the catalysts of Samples 1-4 are provided in Table 1.

TABLE 1

| Sample | Surface Area (m²/g) | Pore Volume (mL/g) | Pore Size (nm) |
|---|---|---|---|
| 1 | 134 | 0.42 | 9.8 |
| 2 | 163 | 0.35 | 13.9 |
| 3 | 147 | 0.51 | 10.3 |
| 4 | 102 | 0.42 | 14.5 |

Figure 3:
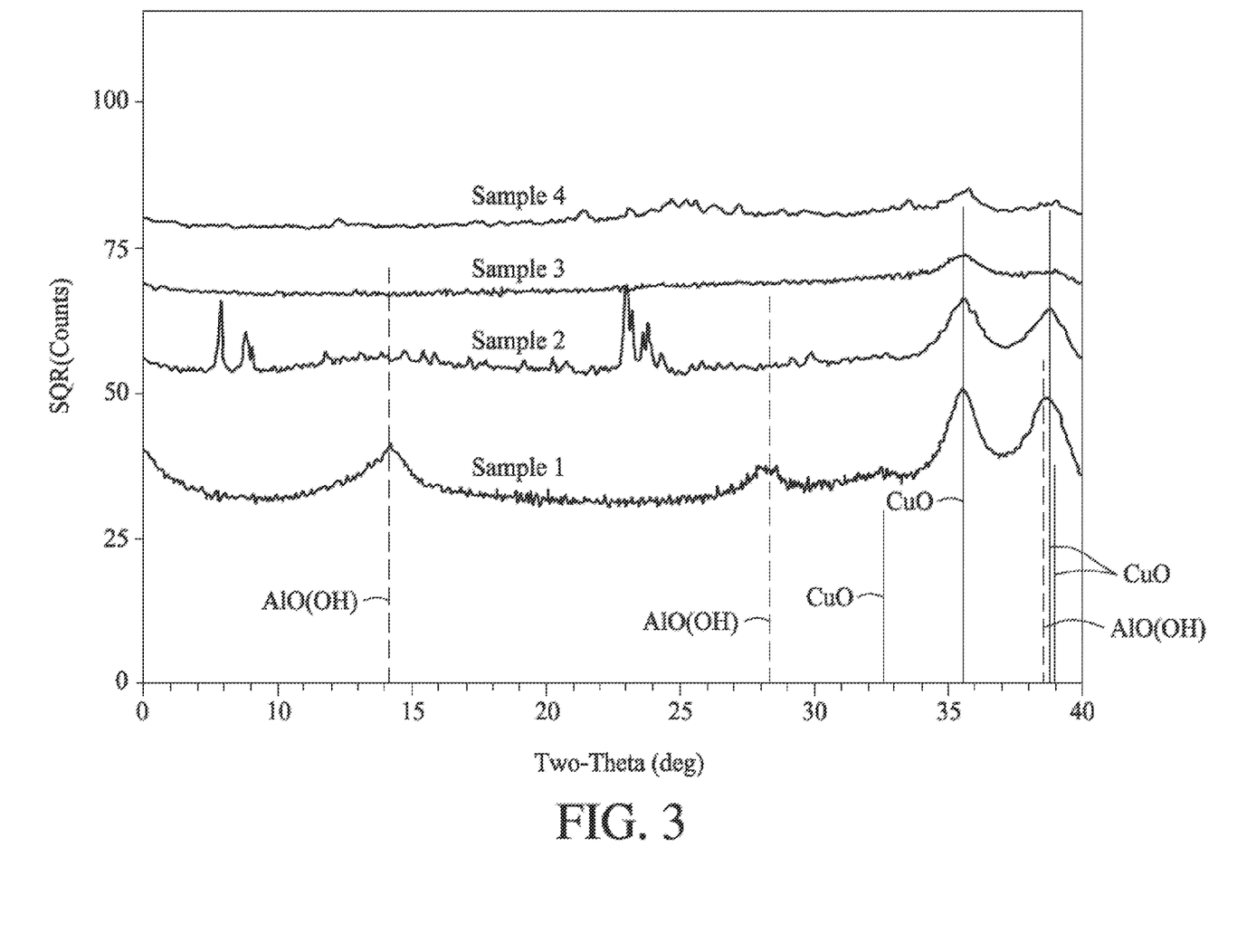
FIG. 3 illustrates the x-ray diffraction (XRD) patterns of the acid/metal bifunctional catalysts of Samples 1-4.

FIG. 3 illustrates the x-ray diffraction (XRD) patterns of the acid/metal bifunctional catalysts of Samples 1-4. Sample 1 has broad XRD peaks identified as CuO and aluminum oxide hydroxide AlOOH. Sample 2 also has broad XRD peaks identified as CuO and characteristic finger prints of ZSM-5. In Sample 3, only a poorly crystallized phase of CuO was detected. The phase of containing phosphotungstic acid is either amorphous or the crystallites are too small to be detected by XRD. In Sample 4, besides a poorly crystallized phase of CuO, there are tiny XRD peaks associated with a poorly crystallized phase of molybdenum oxide and/or molybdenum phosphate.

Catalyst Testing

In separate reactions, a reactor was charged with catalyst samples according to Reference and Samples 1-4 with 125 μm to 160 μm α-$Al_2O_3$ particles above and below the catalyst bed. The catalysts in the reactor were activated by flowing hydrogen at 250° C. over the catalyst bed for 120 minutes. Then, the catalysts were used in a syngas to dimethyl ether reaction under the following conditions: a temperature of 230° C. to 270° C., a pressure of 25 bar to 50 bar, and a gas hourly space velocity (GHSV) of 1,000 $hr^{-1}$ to 8,000 $hr^{-1}$. The reaction feed was 37 vol % to 50 vol % $H_2$, 40 vol % to 50 vol % CO, 13 vol % to 40 vol % $CO_2$, 0 vol % to 3 vol % $CH_4$, 5 vol % to 10 vol % Ar (used as an internal standard), and 0 vol % to 10 vol % of $H_2O$. A gas chromatograph fitted with a flame-ionization detector (FID), a thermal conductivity detector (TCD), and optionally a helium ionization detector (HID) (for low water concentrations of 200 ppm to 2 vol %) was used to analyze the product stream.

Figure 4:
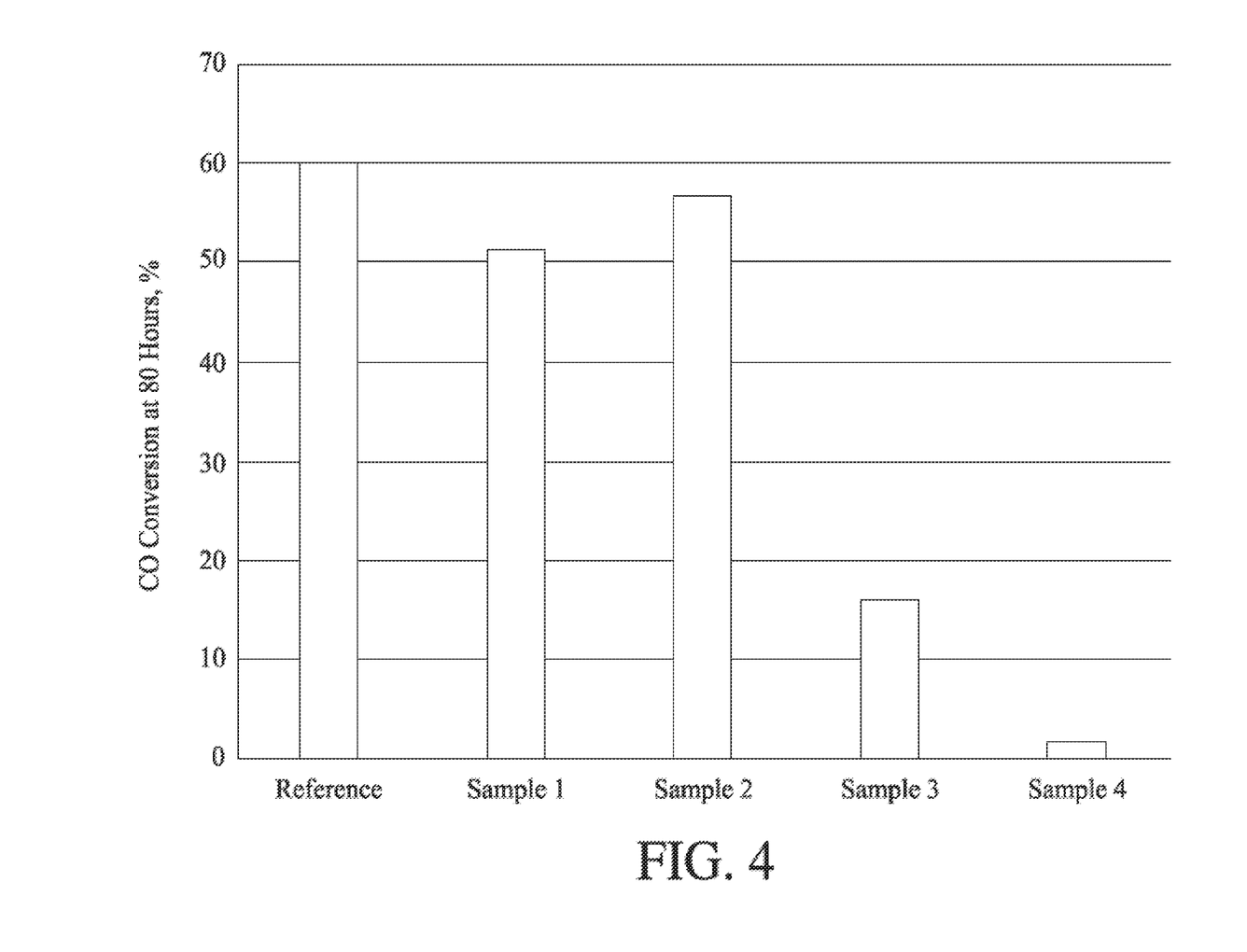
FIG. 4 is a plot of the CO conversion for each of the Reference and Samples 1-4.

FIG. 4 is a plot of the CO conversion for each of the Reference and Samples 1-4 after 80 hours of the catalyst beds being exposed to the reaction feed. At 250° C., 35 bar pressure, and GHSV of 2100 $hr^{-1}$, the CO conversion activity of the Reference catalyst system reached a steady state, around 60%. Sample 1's CO conversion activity is around 52%, which is lower than the reference sample, which may be due to the $Al_2O_3$ coating partially blocking the metal function sites on the CuZnAl. The CO conversion activity of Sample 2 is 57%, which is higher than Sample 1, but it is still slightly lower than the reference catalyst. It seems that the degree of contacts and interactions of metal catalyst and acid catalyst ZSM-5 is closer than the mechanical mixtures in the reference catalyst system of CATAPAL® $Al_2O_3$/CuZnAl. In the Sample 3 and Sample 4, the CO conversion activities are much lower than the reference catalyst, Sample 1, and Sample 2. Sample 3's CO conversion activity is around 16%, and CO conversion on Sample 4 is only around 2%. In Samples 3 and 4, the metal catalyst surface may have been covered by phosphotungstic acid and molybdenum phosphate, which blocked metal function sites for CO conversion.

Figure 5:
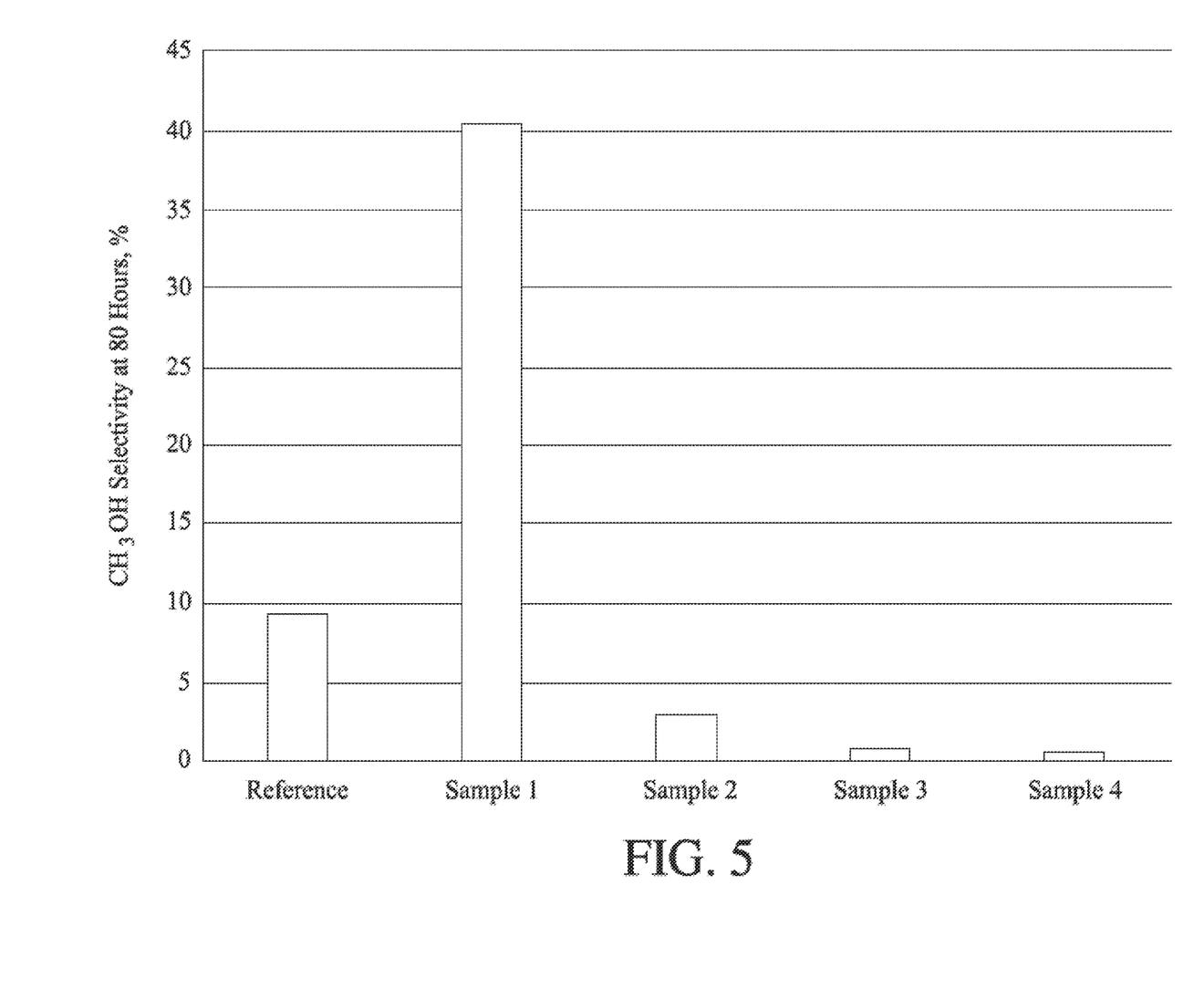
FIG. 5 is a plot of methanol selectivity for each of the Reference and Samples 1-4.

FIG. 5 is a plot of methanol selectivity for each of the Reference and Samples 1-4 after 80 hours of the catalyst beds being exposed to the reaction feed. The Reference catalyst system has about 9.5% methanol selectivity. Sample 1 has methanol selectivity around 40%, which indicates that methanol formed on the CuZnAl catalyst were accumulated on the catalyst system of 25% Al$_2$O$_3$/CuZnAl, instead of immediately being consumed by dehydration to form dimethyl ether. The ratio of acid catalyst in system of 25 wt % CATAPAL® Al$_2$O$_3$/CuZnAl is low. The reaction rate of methanol synthesis on CuZnAl is faster than the dehydration rate of methanol to dimethyl ether on CATAPAL®. Sample 2 has methanol selectivity around 3%, which indicates that most of the methanol formed on the CuZnAl catalyst went through dehydration to form dimethyl ether. Accordingly, acid catalyst of ZSM-5 appears to be more effective for methanol dehydration than CATAPAL®. The reaction rate of methanol synthesis is comparable, or in good match, to the dehydration rate of methanol conversion to dimethyl ether. Sample 3 and Sample 4 have very low methanol selectivities (<1%), which are consistent with low CO conversion activities observed on Sample 3 and Sample 4.

Figure 6:
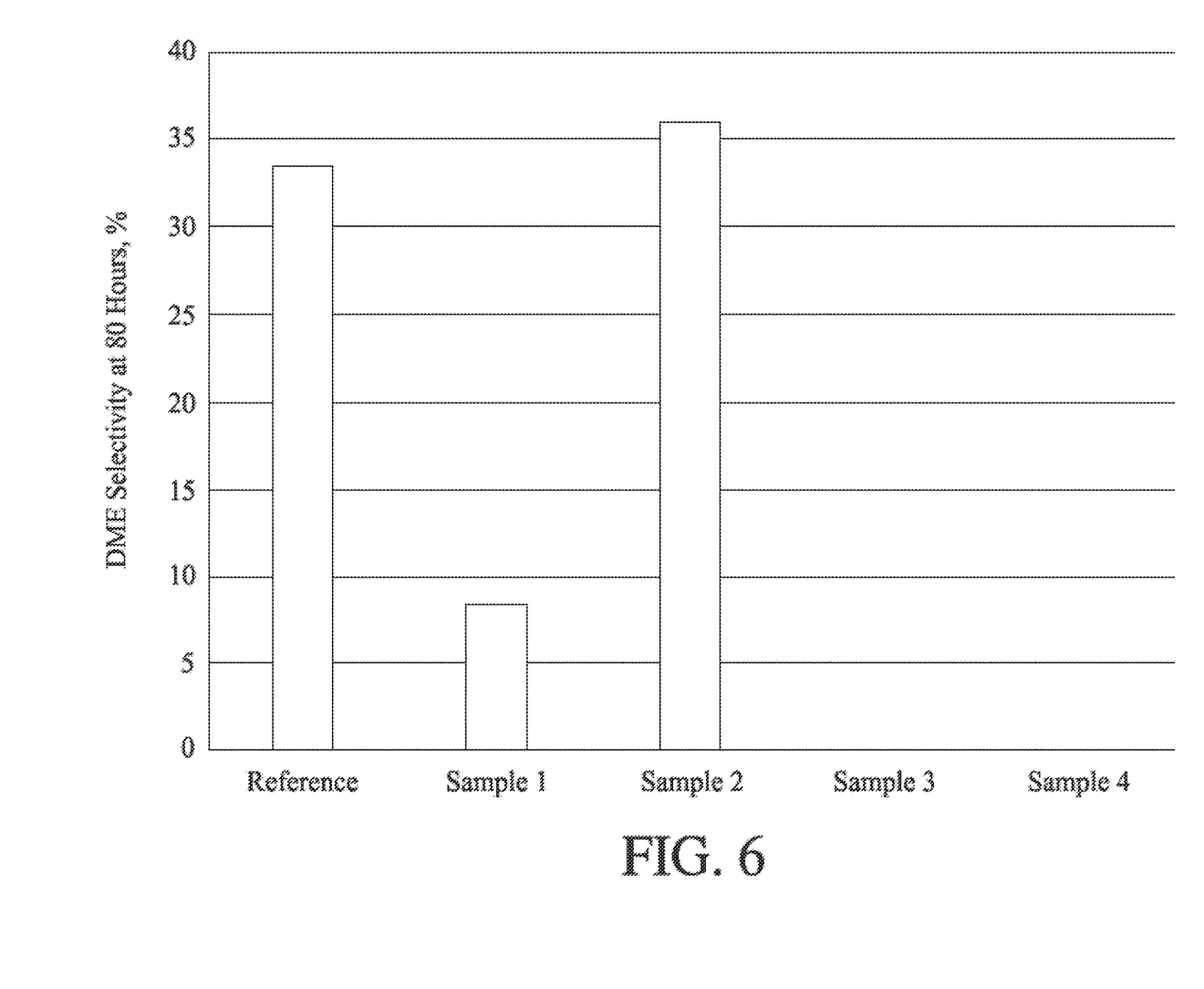
FIG. 6 is a plot of the dimethyl ether selectivity for each of the Reference and Samples 1-4.

FIG. 6 is a plot of the dimethyl ether selectivity for each of the Reference and Samples 1-4 after 80 hours of the catalyst beds being exposed to the reaction feed. The dimethyl ether selectivity of the Reference catalyst is 33.5%. Sample 1 has lower dimethyl ether selectivity, around 8%. Sample 2 has slightly higher dimethyl ether selectivity than the Reference catalyst, around 36%. This indicates that the ZSM-5 catalyst is more effective for the dehydration of methanol to dimethyl ether than CATAPAL®. Sample 3 and Sample 4 have no dimethyl ether selectivities, which are consistent with low CO conversions, and very low methanol selectivities observed on Sample 3 and Sample 4.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
mixing particles of an acid catalyst, particles of a metal catalyst, and a fluid to produce a slurry, wherein the particles of acid catalyst are present at 50 wt % or less relative to a total catalyst weight in the slurry;
heating the slurry;
drying the slurry produce a dried slurry;
producing a powder from the dried slurry; and
calcining the powder to produce an acid/metal bifunctional catalyst,
wherein the particles of acid catalyst comprise zeolite, ion-exchanged zeolite, molecular sieve, or a combination thereof, the particles of acid catalyst having an average diameter of about 1 μm to about 100 μm, and
wherein the particles of metal catalyst comprise Cu, Zn, and Al, the particles of metal catalyst having an average diameter of about 0.01 μm to about 10 μm, the particles of the acid catalyst having a larger average diameter than the particles of the metal catalyst.

2. The method claim 1, wherein producing the powder from the dried slurry comprises:
grinding the dried slurry to produce a powder, wherein the powder comprises 5 wt % or less of the fluid.

3. The method of claim 1, wherein mixing is maintained during heating.

4. The method of claim 1, wherein mixing is performed for 30 minutes to 3 hours.

5. The method of claim 1, wherein heating is to a temperature within 20° C. of a boiling point of the fluid.

6. The method of claim 1, wherein the acid catalyst comprises zeolite, ion exchanged zeolite, or a combination thereof.

7. The method of claim 1, wherein the particles of acid catalyst are present at 10 wt % to 50 wt % relative to the total catalyst weight in the slurry.

8. The method of claim 1, wherein the particles of acid catalyst are present at 15 wt % to 35 wt % relative to the total catalyst weight in the slurry.

9. The method of claim 1, wherein the fluid is selected from the group consisting of: water, methanol, ethanol, alcohols of C1 to C10, oxygenates, and any combination thereof.

10. The method of claim 1, wherein calcining is performed in air at 200° C. to 400° C.

11. The method of claim 1, wherein the acid/metal bifunctional catalyst has an average diameter of 0.01 μm to 100 μm.

12. The method of claim 1, wherein the acid/metal bifunctional catalyst has a N$^2$ BET surface area according to ASTM D3663-03 (2015) of about 75 m$^2$/g to about 200 m$^2$/g.

13. The method of claim 1, wherein the acid/metal bifunctional catalyst has an average pore volume of about 0.1 mL/g to about 1.2 mL/g.

14. The method of claim 1, wherein the acid/metal bifunctional catalyst has an average pore size according to ASTM D4641-17 of about 7 nm to about 17 nm.

15. The method of claim 1 further comprising:
activating the acid/metal bifunctional catalyst in the presence of hydrogen at 150° C. to 350° C.; and
reacting the activated acid/metal bifunctional catalyst with a feedstream comprising hydrogen and carbon monoxide.

16. The method of claim 15, wherein reacting is at a temperature of about 200° C. to about 300° C., a pressure of about 20 bar to about 50 bar, and a gas hourly space velocity (GHSV) of about 1,000 hr$^{-1}$ to about 8,000 hr$^{-1}$.

17. The method of claim 15, Wherein the reacting the activated acid/metal bifunctional catalyst with the feedstream is in the presence of steam.

18. The method of claim 15, wherein reacting the activated acid/metal bifunctional catalyst with the feedstream has a selectivity to producing methanol of 25% to 60%.

19. The method of claim 15, wherein reacting the activated acid/metal bifunctional catalyst with the feedstream has a selectivity to producing dimethyl ether of 20% to 55%.

* * * * *